US012758185B1

(12) United States Patent
Katagiri

(10) Patent No.: US 12,758,185 B1
(45) Date of Patent: Oct. 13, 2026

(54) CART FOR ULTRASOUND DIAGNOSTIC APPARATUS AND ULTRASOUND DIAGNOSTIC UNIT HAVING GAS-SPRING OPERATION MECHANISM

(71) Applicant: FUJIFILM Corporation, Tokyo (JP)

(72) Inventor: Kengo Katagiri, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/078,182

(22) Filed: Mar. 12, 2025

(30) Foreign Application Priority Data

Mar. 22, 2024 (JP) ................................ 2024-045891

(51) Int. Cl.
*A61B 8/00* (2006.01)

(52) U.S. Cl.
CPC .......... *A61B 8/4405* (2013.01); *A61B 8/4411* (2013.01); *A61B 8/4427* (2013.01)

(58) Field of Classification Search
CPC .... A61B 8/4405; A61B 8/4411; A61B 8/4427
See application file for complete search history.

(56) References Cited

U.S. PATENT DOCUMENTS

| | | | | |
|---|---|---|---|---|
| 2013/0300075 A1* | 11/2013 | Arceta | ................. | A61G 12/001 280/33.991 |
| 2017/0027541 A1* | 2/2017 | Henderson | ........... | A61B 8/4405 |
| 2020/0060649 A1* | 2/2020 | Nally | .................. | A61B 8/4433 |

FOREIGN PATENT DOCUMENTS

| | | |
|---|---|---|
| JP | 2010057886 | 3/2010 |

* cited by examiner

*Primary Examiner* — Serkan Akar
(74) *Attorney, Agent, or Firm* — JCIPRNET

(57) ABSTRACT

A cart with a table is provided. The cart includes a movement transmission mechanism that transmits movement of a user push-button being pressed to a gas spring so that the table is unlocked and enters an unlocked state. The movement transmission mechanism includes a translational movement component. The cart includes an apparatus push-button that is pressed by a transportable ultrasound diagnostic apparatus in a case where the transportable ultrasound diagnostic apparatus is placed on the table and a movement restriction portion that is interlocked with the apparatus push-button. The movement restriction portion restricts movement of the translational movement component in a case where the apparatus push-button is in an unpressed state and allows the movement of the translational movement component in a case where the apparatus push-button is in a pressed state.

8 Claims, 12 Drawing Sheets

CART FOR ULTRASOUND DIAGNOSTIC APPARATUS AND ULTRASOUND DIAGNOSTIC UNIT HAVING GAS-SPRING OPERATION MECHANISM

CROSS-REFERENCE TO RELATED APPLICATION

This application claims priority under 35 USC 119 from Japanese Patent Application No. 2024-045891, filed 22 Mar. 2024, the disclosure of which is incorporated by reference herein.

BACKGROUND OF THE INVENTION

1. Field of the Invention

The present disclosure relates to a cart for an ultrasound diagnostic apparatus and an ultrasound diagnostic unit, and particularly to a technology for adjustment of the height of a cart table.

2. Description of the Related Art

In ultrasound examination of a living body, an ultrasound diagnostic apparatus is used. The ultrasound diagnostic apparatus is a medical apparatus that generates and displays an ultrasound image based on a received signal that is obtained through transmission and reception of ultrasound waves. A tomographic image is known as a representative ultrasound image.

Transportable ultrasound diagnostic apparatuses are being used. Examples of such ultrasound diagnostic apparatuses include a laptop type ultrasound diagnostic apparatus, which can be carried in a user's hand. In addition, the transportable ultrasound diagnostic apparatuses are often used after being placed on a cart. A laptop type transportable ultrasound diagnostic apparatus is moved to a position right beside a subject after being placed on a cart and the ultrasound diagnostic apparatus is opened and operated in a state where the ultrasound diagnostic apparatus is placed on the cart such that a probe is extended up to a subject and ultrasound waves are transmitted and received to and from the subject.

Disclosed in JP2010-57886A is, in relation to a carriage for a portable ultrasound diagnostic apparatus, a configuration in which it is possible to activate a gas spring and to raise a placement portion by pulling a wire connected to the gas spring by using a control rod in a case where a portable ultrasound diagnostic apparatus is on the placement portion.

SUMMARY OF THE INVENTION

It is conceivable to provide a gas spring and a user push-button for a cart including a table on which a transportable ultrasound diagnostic apparatus is placed. The gas spring can form a locked state in which the table is unraisable and unlowerable and an unlocked state in which the table is unlocked and is biased upward. In a case where the user push-button is pressed, the gas spring is operated such that the state of the table is changed from the locked state to the unlocked state. It is conceivable that the table is powerfully raised against the intention of a user in a case where the user push-button is pressed in a state where the transportable ultrasound diagnostic apparatus is not on the table in a configuration as described above since the weight of the apparatus is not applied to the table.

Therefore, an object of the present disclosure is to prevent a table from being rapidly raised against the intention of a user in relation to a cart for an ultrasound diagnostic apparatus or an ultrasound diagnostic unit.

According to an aspect of the present disclosure, there is provided a cart for an ultrasound diagnostic apparatus with a table on which a transportable ultrasound diagnostic apparatus is placed, the cart comprising a gas spring that is able to form a locked state in which the table is unraisable and unlowerable and an unlocked state in which the table is unlocked and is biased upward. The gas spring includes a gas spring operation reception portion that receives an operation of switching between the locked state and the unlocked state. The cart further includes a user push-button and a movement transmission mechanism that transmits movement of the user push-button being pressed to the gas spring operation reception portion so that a state of the table is changed from the locked state to the unlocked state in a case where the user push-button is pressed. The movement transmission mechanism includes a translational movement component that translationally moves as the user push-button is pressed and that is in charge of at least part of transmission of the movement from the user push-button to the gas spring operation reception portion. The cart further includes an apparatus push-button that is provided to protrude from an upper surface of the table and that is pressed by the transportable ultrasound diagnostic apparatus in a case where the transportable ultrasound diagnostic apparatus is placed on the table and a movement restriction portion that is interlocked with the apparatus push-button. The movement restriction portion restricts movement of the translational movement component while being positioned in a region in which the movement restriction portion interferes with the movement of the translational movement component in a case where the apparatus push-button is in an unpressed state and allows the movement of the translational movement component while being positioned in a region in which the movement restriction portion does not interfere with the movement of the translational movement component in a case where the apparatus push-button is in a pressed state.

According to an aspect of the present disclosure, there is provided an ultrasound diagnostic unit comprising the above-described cart for an ultrasound diagnostic apparatus and the transportable ultrasound diagnostic apparatus placed on the table of the cart.

According to the present disclosure, movement of the translational movement component which is caused in a case where the user push-button is pressed is restricted and the movement of the translational movement component is not transmitted to the gas spring operation reception portion in a state where the transportable ultrasound diagnostic apparatus is not placed on the table. Therefore, the table can be prevented from being rapidly raised.

DESCRIPTION OF THE PREFERRED EMBODIMENTS

Figure 1:
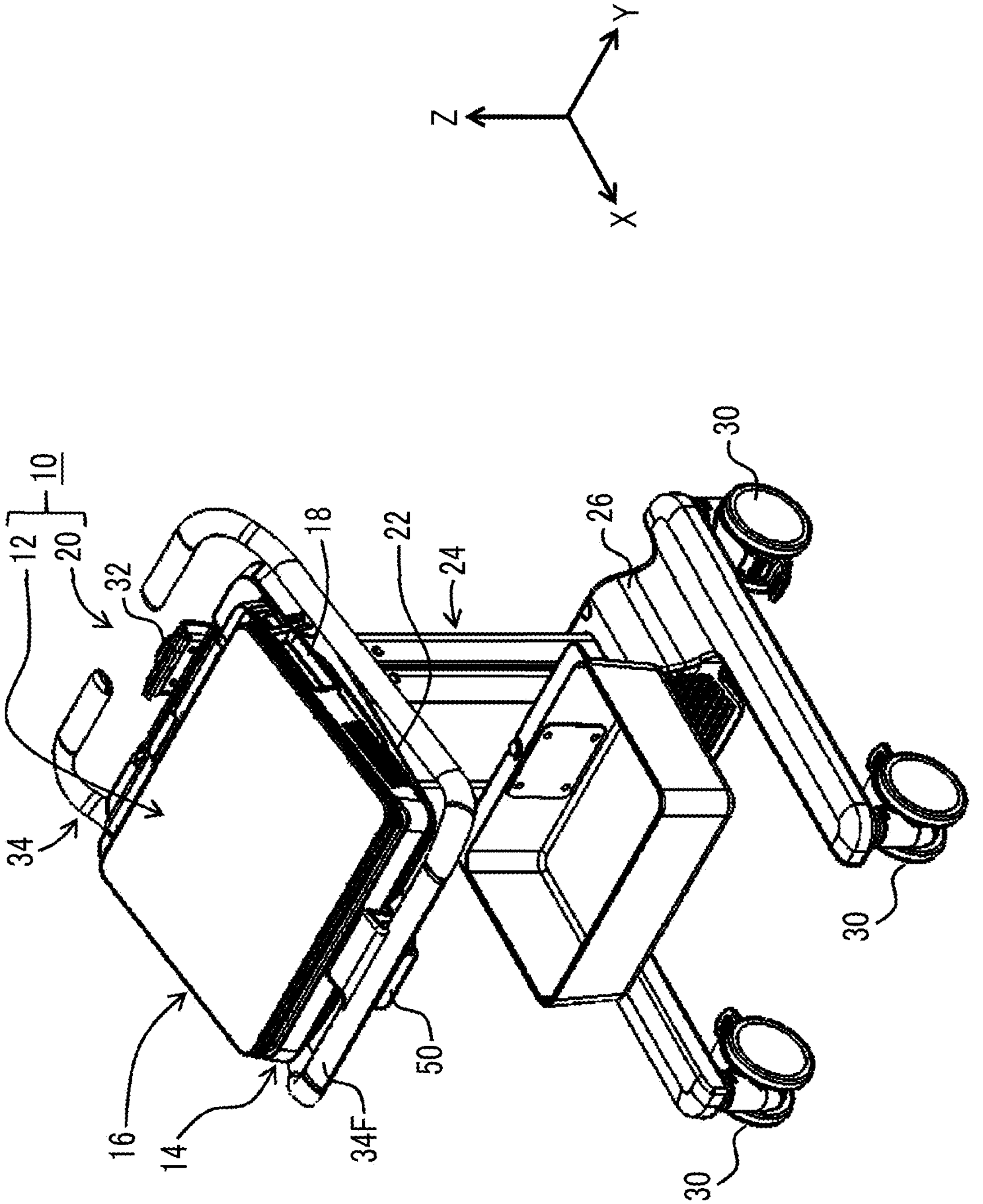
FIG. 1 is a perspective view showing an ultrasound diagnostic unit according to an embodiment.

Hereinafter, an embodiment will be described with reference to the drawings. The present disclosure is not limited to the embodiment described herein. In all of the drawings, the same elements are denoted by the same reference numerals and the description thereof will not be repeated. In this specification, unless otherwise specified, directions represented by arrows X, Y, and Z in FIG. 1 will be referred to as "a forward direction", "a rightward direction", and "an upward direction", and directions opposite thereto will be referred to as "a rearward direction", "a leftward direction", and "a downward direction". A direction along the arrow Z coincides with a direction in which the gravity acts, that is, a vertical direction.

(1) Outline of Embodiment

A cart for an ultrasound diagnostic apparatus according to an embodiment includes a table on which a transportable ultrasound diagnostic apparatus is placed and a gas spring. The gas spring is able to form a locked state in which the table is unraisable and unlowerable and an unlocked state in which the table is unlocked and is biased upward. The gas spring includes a gas spring operation reception portion that receives an operation of switching between the locked state and the unlocked state. The cart includes a user push-button and a movement transmission mechanism. The movement transmission mechanism transmits movement of the user push-button being pressed to the gas spring operation reception portion so that a state of the table is changed from the locked state to the unlocked state in a case where the user push-button is pressed. The movement transmission mechanism includes a translational movement component that translationally moves as the user push-button is pressed and that is in charge of at least part of transmission of the movement from the user push-button to the gas spring operation reception portion. The cart includes an apparatus push-button and a movement restriction portion. The apparatus push-button is provided to protrude from an upper surface of the table and that is pressed by the transportable ultrasound diagnostic apparatus in a case where the transportable ultrasound diagnostic apparatus is placed on the table. The movement restriction portion is interlocked with the apparatus push-button. Specifically, the movement restriction portion restricts movement of the translational movement component while being positioned in a region in which the movement restriction portion interferes with the movement of the translational movement component in a case where the apparatus push-button is in an unpressed state and allows the movement of the translational movement component while being positioned in a region in which the movement restriction portion does not interfere with the movement of the translational movement component in a case where the apparatus push-button is in a pressed state.

According to a configuration as described above, the apparatus push-button is in the unpressed state in a case where the transportable ultrasound diagnostic apparatus is not placed on the table and in such a state, movement of the translational movement component which is caused in a case where the user push-button is pressed is restricted by the movement restriction portion and the movement of the translational movement component is not transmitted to the gas spring operation reception portion. Therefore, in a case where the transportable ultrasound diagnostic apparatus is not placed on the table, an operation performed on the user push-button has no effect and the table can be prevented from being rapidly raised against the intention of a user.

Note that the movement transmission mechanism may include one or more mechanical elements and may transmit movement, which is caused in a case where the apparatus push-button is pressed, to the gas spring operation reception portion after changing the direction of the movement once or more. Examples of the one or more mechanical elements include a rod, a bell crank, a rack and pinion, a gear, a cam, a wire, and the like. The movement transmission mechanism may include a mechanism that converts linear movement into rotational movement, a mechanism that converts rotational movement into linear movement, and the like. In addition, the gas spring operation reception portion may be, for example, a button employed for a gas spring in the related art. However, the form thereof is not limited.

In the embodiment, the user push-button is disposed in front of the table.

According to a configuration as described above, a user can easily access the user push-button since the user (for example, an operator) is generally in front of the table.

In the embodiment, a front handle that is connected to the table and that is positioned in front of the table is provided. The user push-button is disposed below a center of the front handle in a lateral direction.

According to a configuration as described above, a user (for example, an operator) can cause the table to enter the unlocked state by pressing the user push-button with a thumb in a state where a hand is placed on a left portion or a right portion of the front handle. In addition, for example, the user also can cause the table to enter the unlocked state by pressing the user push-button with the thumbs of both hands in a state where both hands are placed on the right and left portions of the front handle.

In the embodiment, the translational movement component includes a protruding portion that protrudes in a direction intersecting a movement direction of the translational movement component. The cart includes a swinging body that is swingable around a support shaft. The swinging body includes the apparatus push-button provided on one side with respect to the support shaft and includes the movement restriction portion provided on a side opposite to the one side with respect to the support shaft. The swinging body forms the unpressed state of the apparatus push-button by being biased in a certain rotation direction around the support shaft by a biasing member. In a case where the apparatus push-button is in the unpressed state, the apparatus push-button protrudes from the upper surface of the table and the movement restriction portion restricts movement of the protruding portion of the translational movement component while being positioned in a region in which the movement restriction portion interferes with the movement of the protruding portion. In a case where the swinging body swings as the apparatus push-button is pressed, the movement restriction portion allows the movement of the protruding portion of the translational movement component while being positioned in a region in which the movement restriction portion does not interfere with the movement of the protruding portion.

According to a configuration as described above, since the apparatus push-button and the movement restriction portion are realized by the swinging body, the structure can be simplified.

In the embodiment, the translational movement component includes a protruding portion that protrudes in a direction intersecting a movement direction of the translational movement component. The cart includes a moving body that is movable in a vertical direction. The moving body is connected to the apparatus push-button and includes the movement restriction portion. The moving body forms the unpressed state of the apparatus push-button by being biased upward by a biasing member. In a case where the apparatus push-button is in the unpressed state, the apparatus push-button protrudes from the upper surface of the table and the movement restriction portion restricts movement of the protruding portion of the translational movement component while being positioned in a region in which the movement restriction portion interferes with the movement of the protruding portion. In a case where the moving body is lowered as the apparatus push-button is pressed, the movement restriction portion allows the movement of the protruding portion of the translational movement component while being positioned in a region in which the movement restriction portion does not interfere with the movement of the protruding portion.

According to a configuration as described above, the apparatus push-button and the movement restriction portion can be realized in a narrow space extending in the vertical direction.

In the embodiment, the user push-button is disposed in front of the table. The movement transmission mechanism and the gas spring operation reception portion are disposed in an inner space of the table. The gas spring operation reception portion is a gas spring button that protrudes upward. The movement transmission mechanism includes a movement direction changing mechanism that converts forward movement of the translational movement component, which is caused in a case where the user push-button is pressed, into downward movement and that transmits the downward movement to the gas spring button.

According to a configuration as described above, transmission of movement from the user push-button to the gas spring button can be realized with a simple structure.

In the embodiment, a columnar support that supports the table to be raisable and lowerable is provided. The gas spring is disposed in the columnar support. The columnar support includes an upper columnar support to which the table is connected and a lower columnar support that is disposed below the upper columnar support. The columnar support expands and contracts as one of the upper columnar support or the lower columnar support is inserted into the other of the upper columnar support or the lower columnar support. One end of the gas spring is fixed to the table and the other end of the gas spring is fixed to the lower columnar support or a support body disposed below the lower columnar support. The one end of the gas spring includes the gas spring button that is disposed in the inner space of the table.

According to a configuration as described above, expansion and contraction of the table can be realized with a simple structure.

An ultrasound diagnostic unit according to the embodiment includes the above-described cart for an ultrasound diagnostic apparatus and the transportable ultrasound diagnostic apparatus placed on the table of the cart.

(2) Details of Embodiment

FIG. 1 shows an ultrasound diagnostic unit 10 according to the embodiment. The ultrasound diagnostic unit 10 is a medical unit that is used in a case where ultrasound examination is performed in a medical institution. The ultrasound diagnostic unit 10 is composed of a transportable ultrasound diagnostic apparatus 12 and a cart 20. The transportable ultrasound diagnostic apparatus 12 (hereinafter, will be simply referred to as the ultrasound diagnostic apparatus 12) is attachably and detachably mounted onto a table 22 of the cart 20. The ultrasound diagnostic apparatus 12 is used with an ultrasound probe (not shown) connected thereto. The ultrasound diagnostic apparatus 12 has a form like a notebook PC or the like. Specifically, the ultrasound diagnostic apparatus 12 is composed of a body 14 and a display 16. The body 14 and the display 16 are connected to each other by a hinge. Generally, a user operates the ultrasound diagnostic apparatus 12 at a position in front of the ultrasound diagnostic apparatus 12.

The cart 20 includes the table 22 on which the ultrasound diagnostic apparatus 12 is placed. The table 22 is a member that supports the ultrasound diagnostic apparatus 12. The table 22 is slightly inclined with respect to an XY plane. The angle of inclination thereof falls, for example, in a range of 8 to 12 degrees. A right side surface of the body 14 is provided with a connector 18. A connector of the ultrasound probe is attachably and detachably connected to the connector 18. The ultrasound probe transmits an ultrasound wave to a living body and receives a reflected wave from the living body.

The body 14 includes a case. A plurality of electronic circuits are provided in the case. The plurality of electronic circuits include a reception circuit, a transmission circuit, a processor, and the like. The processor functions as a generator that generates an ultrasound image based on a received signal that is acquired through transmission and reception of ultrasound waves. The display 16 is composed of a liquid crystal display (LCD), an organic LED display (OLED), or the like. In the case of ultrasound examination, an ultrasound image is displayed on the display 16 that is in an opened state.

Figure 2:
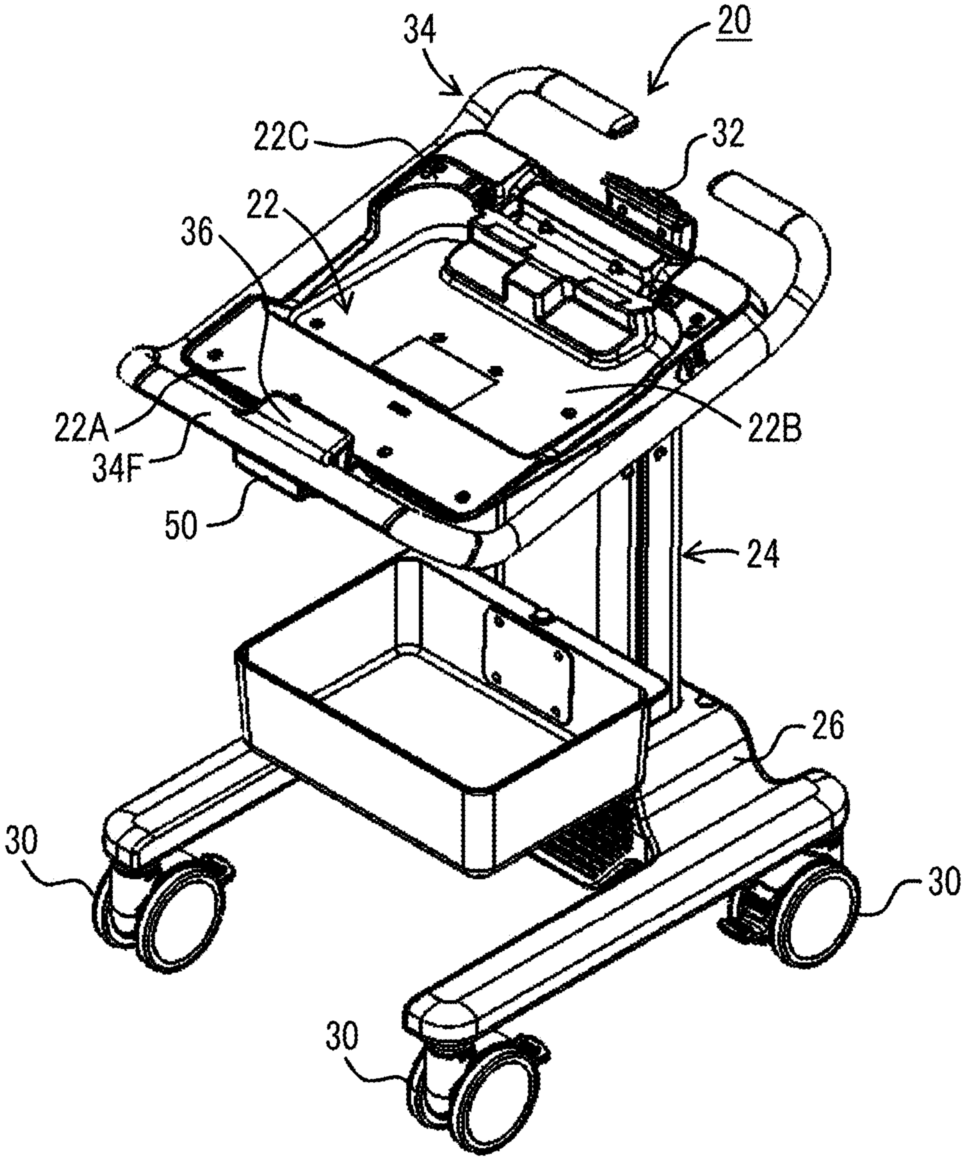
FIG. 2 is a perspective view showing a contraction state of a cart for an ultrasound diagnostic apparatus according to the embodiment.
Figure 3:
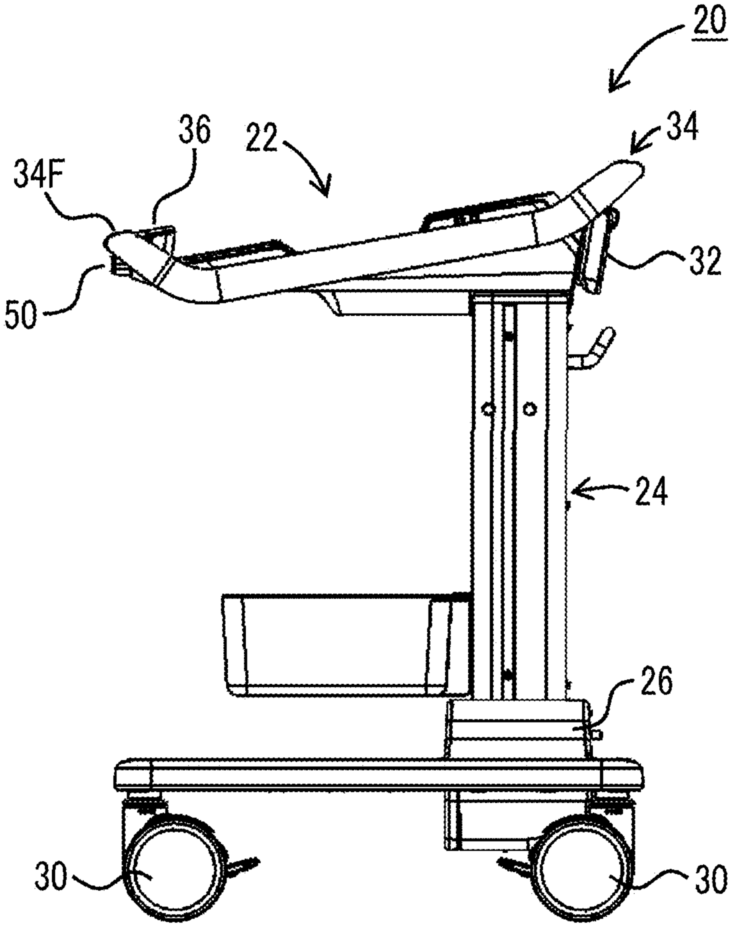
FIG. 3 is a side view showing the contraction state of the cart for an ultrasound diagnostic apparatus according to the embodiment.
Figure 4:
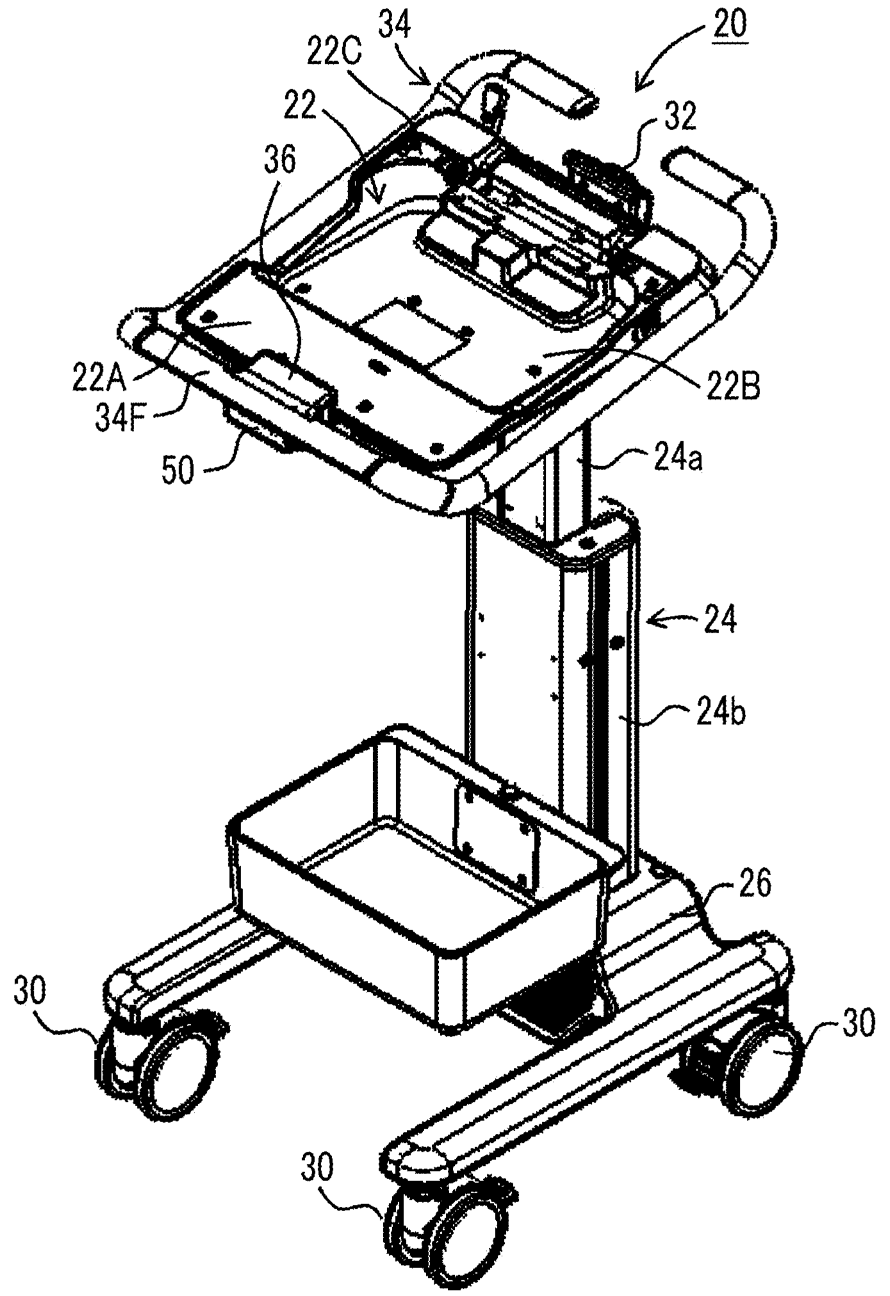
FIG. 4 is a perspective view showing an expansion state of the cart for an ultrasound diagnostic apparatus according to the embodiment.
Figure 5:
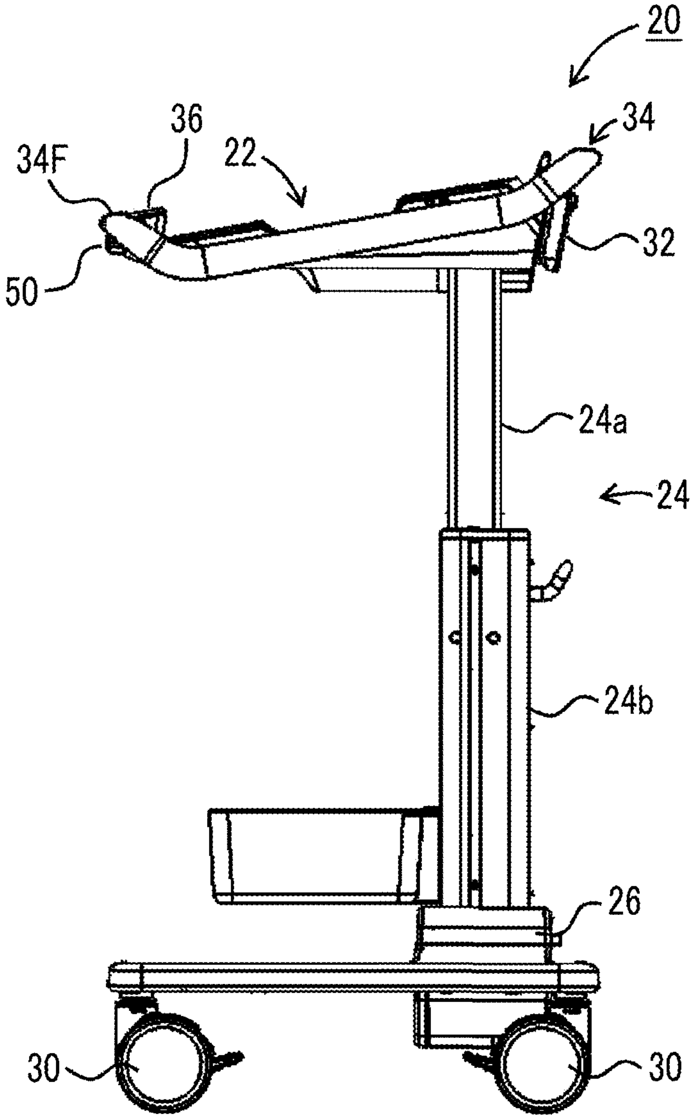
FIG. 5 is a side view showing the expansion state of the cart for an ultrasound diagnostic apparatus according to the embodiment.

FIGS. 2 to 5 are views showing the cart 20, FIGS. 2 and 3 show a contraction state of a columnar support 24 and FIGS. 4 and 5 show an expansion state of the columnar support 24. The cart 20 includes a support body 26 and the columnar support 24. The support body 26 is provided with four casters 30. The support body 26 supports the columnar support 24. The columnar support 24 has a function of expanding and contracting. The columnar support 24 supports the table 22.

As shown in FIG. 2, the table 22 includes a front portion 22A, an intermediate portion 22B, and a rear portion 22C. The intermediate portion 22B is recessed. The ultrasound diagnostic apparatus 12 is placed on the front portion 22A and the rear portion 22C. A handle 34 is provided to surround the table 22. The handle 34 is fixed to the table 22 by a plurality of connecting members. One of the plurality of connecting members is a front block 36. The handle 34 includes a front handle 34F. The front handle 34F is connected to the table 22 by the front block 36. The front handle 34F is positioned in front of the table 22 and extends in a lateral direction.

Figure 6:
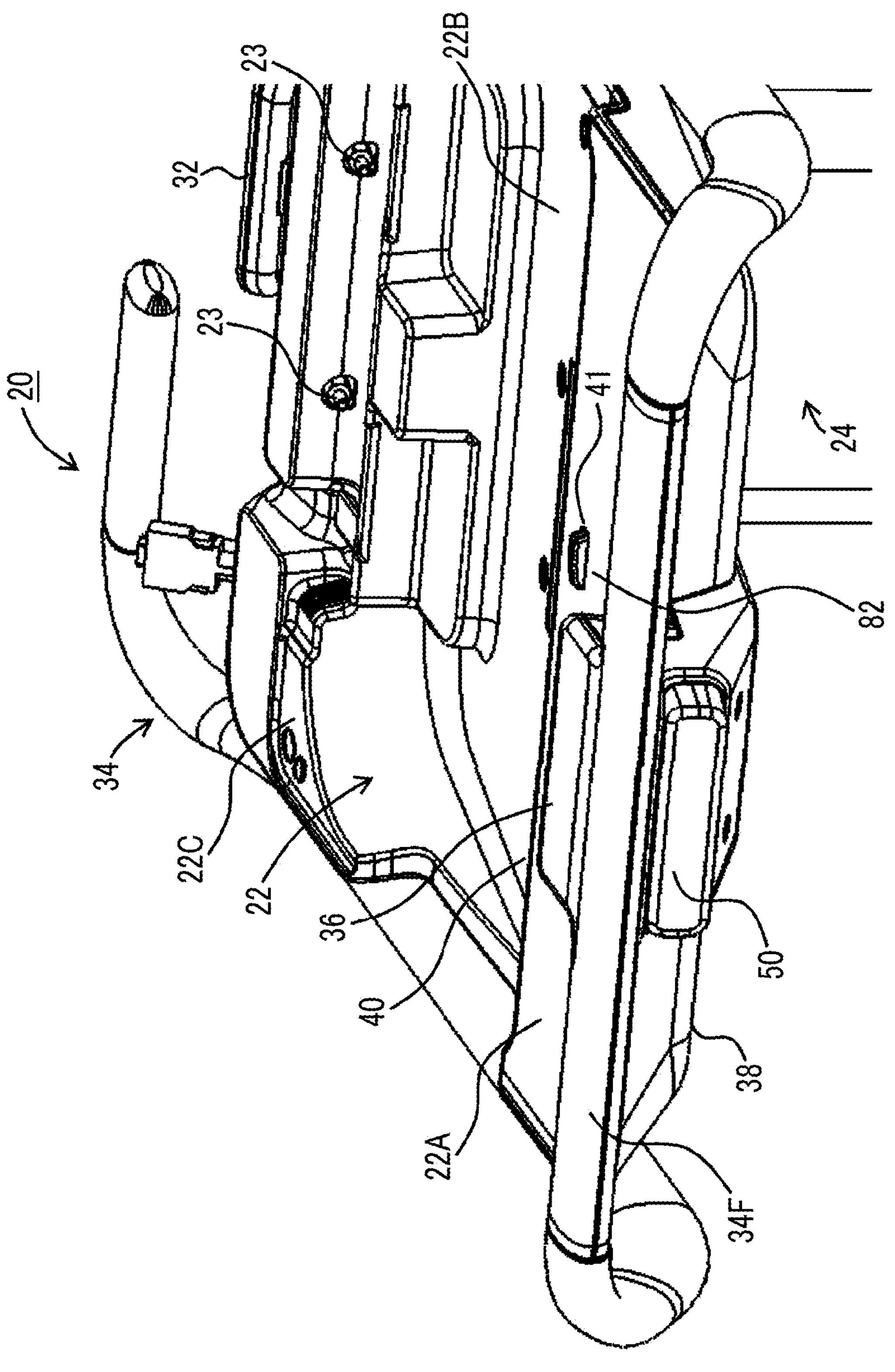
FIG. 6 is a perspective view showing a portion of a table.
Figure 7:
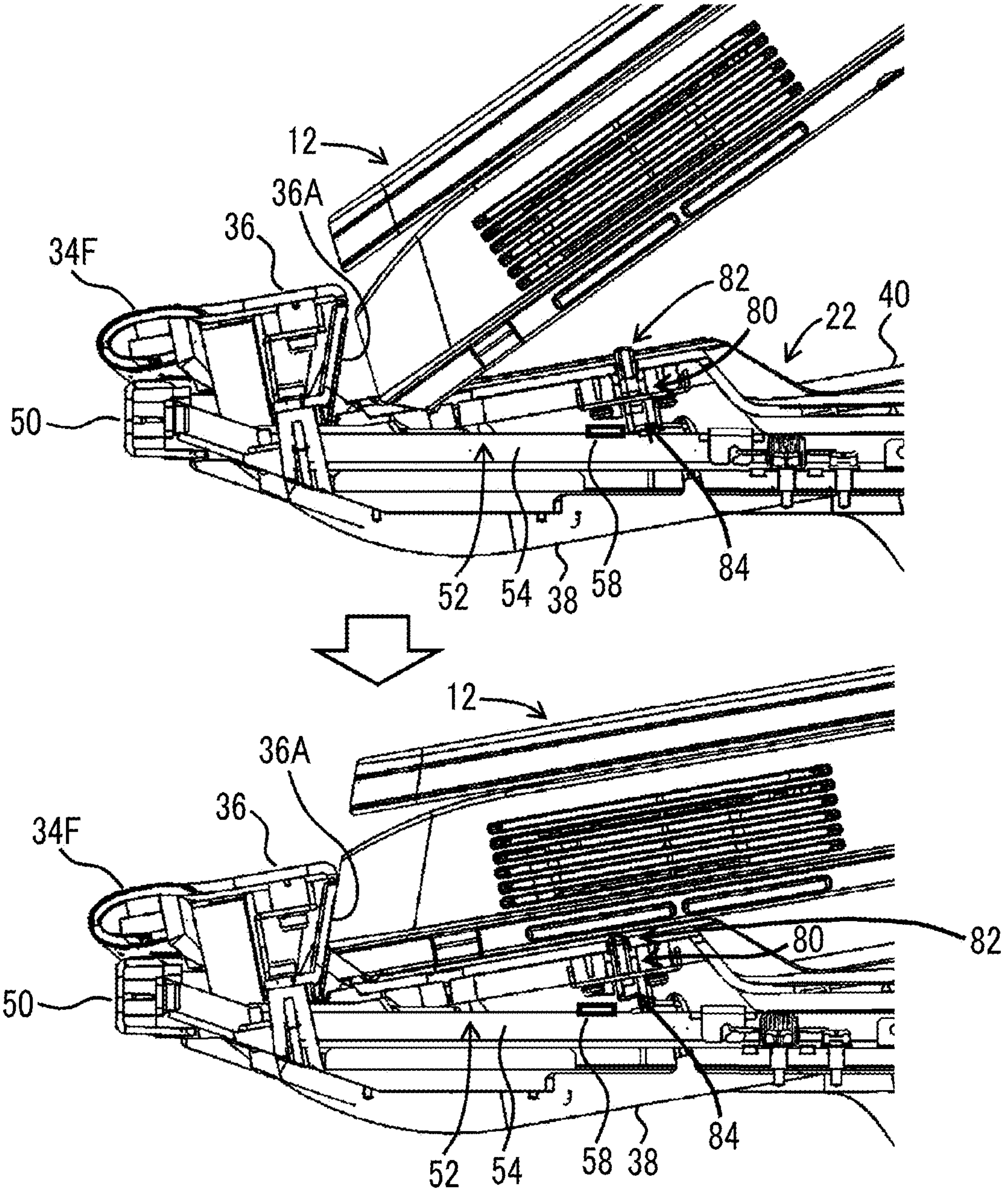
FIG. 7 is a view showing a configuration of a front portion of the table and shows a process in which the ultrasound diagnostic apparatus is placed.

As shown in FIG. 6, the front block 36 is provided at a front portion of the table 22. As shown in FIG. 7, a rear surface 36A of the front block 36 is a holding surface. A front portion of the ultrasound diagnostic apparatus 12 abuts the rear surface 36A and the front portion of the ultrasound diagnostic apparatus 12 is held by the front block 36 in such a state.

As shown in FIG. 3, a rear portion of the cart 20 is provided with a binding operation portion 32 used to bind the ultrasound diagnostic apparatus to the table 22. The binding operation portion 32 is a member having a substantially rectangular shape as seen in a rear view and a lower portion of the binding operation portion 32 is provided with a rotational movement shaft extending in the lateral direction. The binding operation portion 32 rotationally moves around the rotational movement shaft to switch between a non-binding state in which an upper portion of the binding operation portion 32 is separated from a rear surface of the table 22 and a binding state in which the upper portion is close to the rear surface of the table 22.

In a case where the ultrasound diagnostic apparatus 12 is to be mounted to the table 22, first, the binding operation portion 32 is caused to enter the non-binding state. Then, as shown in the upper drawing of FIG. 7, a rear portion of the ultrasound diagnostic apparatus 12 is placed on the table 22 (refer to the lower drawing of FIG. 7) in a state where a front portion of the ultrasound diagnostic apparatus 12 is inclined downward and the front portion is aligned with a specified position of a front portion of the table 22. Thereafter, the state of the binding operation portion 32 is changed from the non-binding state to the binding state. In a case where the state of the binding operation portion 32 is changed from the non-binding state to the binding state, two pins 23 (refer to FIG. 6) protrude toward a front side from the rear portion of the table 22 and the two pins 23 are inserted into two holes provided in a rear surface of the ultrasound diagnostic apparatus 12. Accordingly, the rear portion of the ultrasound diagnostic apparatus 12 is bound to the table 22.

As shown in FIG. 5, the columnar support 24 supports the table 22 to be raisable and lowerable. The columnar support 24 includes an upper columnar support 24*a* to which the table 22 is connected and a lower columnar support 24*b* that is disposed below the upper columnar support 24*a*. The upper columnar support 24*a* is smaller than the lower columnar support 24*b* in width in the lateral direction and thickness in a front-rear direction. The columnar support 24 contracts as the upper columnar support 24*a* is inserted into the lower columnar support 24*b* and expands as the upper columnar support 24*a* exits the lower columnar support 24*b*.

Figure 8:
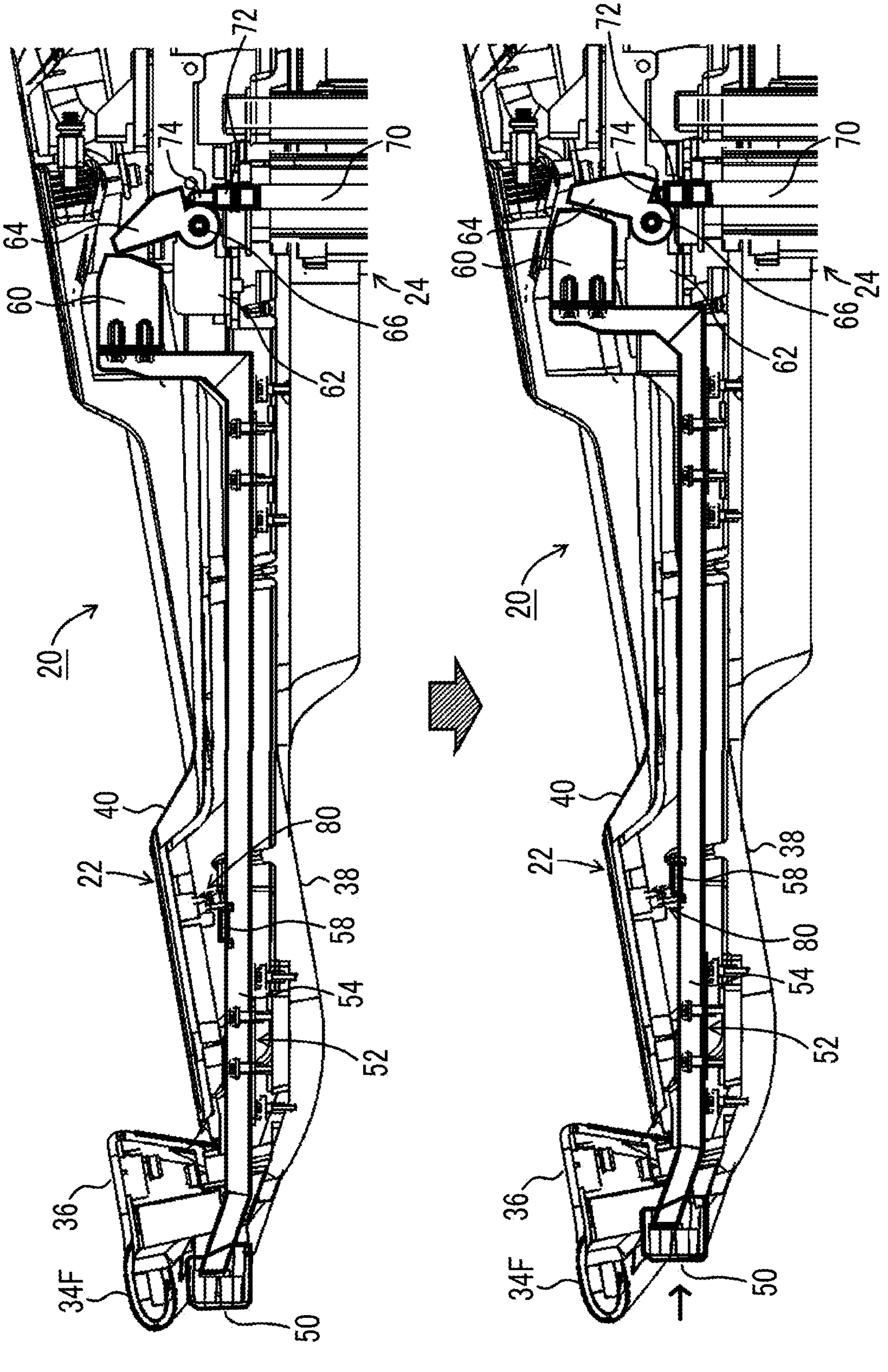
FIG. 8 shows cross-sectional views showing the inside of the table and shows a state before the pressing of a user push-button and a state after the pressing of the user push-button.
Figure 9:
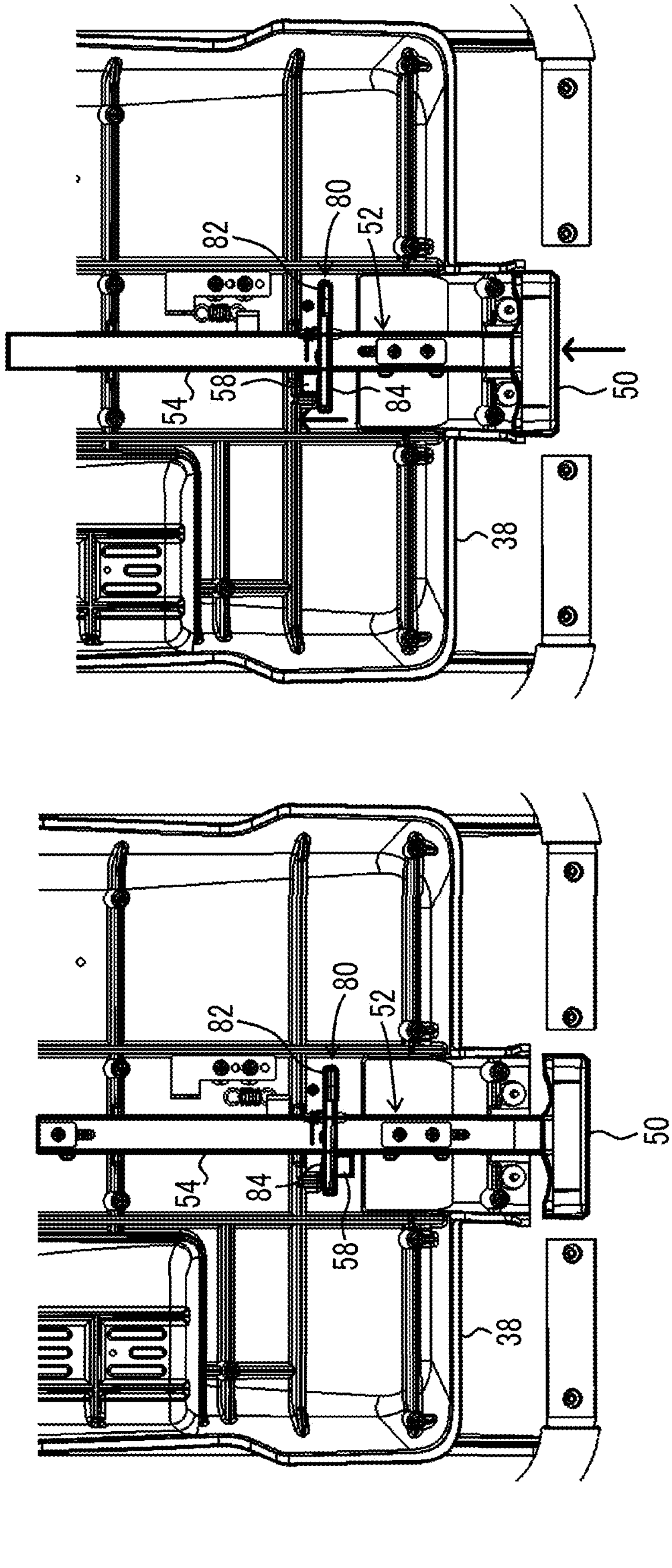
FIG. 9 shows top views showing the inside of the table and shows a state before the pressing of the user push-button and a state after the pressing of the user push-button.

As shown in FIG. 6, the cart 20 includes a user push-button 50 for an operation of raising and lowering the table 22. FIG. 8 is a cross-sectional view showing the inside of the table 22, in which the upper drawing shows the user push-button 50 in an unpressed state and the lower drawing shows the user push-button 50 in a pressed state. FIG. 9 is a top view showing the inside of the table 22, in which a left drawing shows the user push-button 50 in the unpressed state and a right drawing shows the user push-button 50 in the pressed state.

As shown in FIG. 8, the cart 20 includes a gas spring 70 disposed inside the columnar support 24. One end 72 of the gas spring 70 is fixed to the table 22, and the other end of the gas spring 70 is fixed to the lower columnar support 24*b* (refer to FIG. 5) or the support body 26 disposed below the lower columnar support 24*b*. The one end 72 (refer to FIG. 8) of the gas spring 70 includes a gas spring button 74 serving as a gas spring operation reception portion that is disposed in an inner space of the table 22. The gas spring button 74 protrudes upward and is biased upward.

The gas spring 70 can form a locked state in which the table 22 is unraisable and unlowerable (the columnar support 24 is locked to be unexpandable and uncontractable) and an unlocked state in which the table 22 is unlocked and is biased upward (so that the columnar support 24 expands). The gas spring button 74 receives an operation of switching between the locked state and the unlocked state. Specifically, the table 22 enters the locked state in a case where the gas spring button 74 enters an unpressed state and the table 22 enters the unlocked state in a case where the gas spring button 74 enters a pressed state.

The table 22 includes a housing 38 and a top plate 40 attached to the housing 38. The table 22 includes the inner space provided between the housing 38 and the top plate 40. A mechanism provided to raise and lower the table 22 is disposed in the inner space of the table 22. Specifically, the cart 20 includes a movement transmission mechanism 52 disposed in the inner space of the table 22. The movement transmission mechanism 52 transmits movement of the user push-button 50 being pressed to the gas spring button 74 so that the state of the table 22 is changed from the locked state to the unlocked state in a case where the user push-button 50 is pressed.

The movement transmission mechanism 52 includes a translational movement component 54, a tip portion 60, and a swinging body 64 for the gas spring button 74. The translational movement component 54 extends in the front-rear direction. The user push-button 50 is connected to one end of the translational movement component 54. The user push-button 50 protrudes forward from an opening provided in the housing 38. The tip portion 60 is connected to the other end of the translational movement component 54.

The cart 20 includes a holding portion 62 fixed to the housing 38. The swinging body 64 is held by the holding portion 62 to swing around a support shaft 66. The swinging body 64 is a movement direction changing mechanism that converts forward movement of the translational movement component 54, which is caused in a case where the user push-button 50 is pressed, into downward movement and transmits the downward movement to the gas spring button 74.

As shown in the upper drawing of FIG. 8, the swinging body 64 at an initial position is inclined forward since a bottom wall of the swinging body 64 is lifted by the gas spring button 74. In a case where the user push-button 50 is pressed, as shown in the lower drawing of FIG. 8, the translational movement component 54 moves forward and the tip portion 60 presses a front wall of the swinging body 64. Accordingly, the swinging body 64 swings and the bottom wall of the swinging body 64 presses the gas spring button 74, so that the state of the gas spring 70 is changed to an operative state. Accordingly, the table 22 enters the unlocked state.

In a case where the user push-button 50 enters the unpressed state (in a case where a user separates a hand from the user push-button 50), the bottom wall of the swinging body 64 is lifted by an upward biasing force of the gas spring button 74 as shown in the upper drawing of FIG. 8 and the front wall of the swinging body 64 presses the tip portion 60 to a rear side. Accordingly, the translational movement component 54 moves backward and the user push-button 50 returns to the initial position. The gas spring 70 enters a non-operative state and the table 22 enters the locked state.

As described above, in a case where the user push-button 50 is pressed, the gas spring button 74 is moved such that the state of the table 22 is changed from the locked state to the unlocked state. Since the table 22 enters the unlocked state and is biased upward in a case where the user push-button 50 is operated, a user can raise the table 22 only by operating the user push-button 50 or by lightly lifting the table 22 while operating the user push-button 50. In addition, a user can lower the table 22 by operating the user push-button 50 and pressing the table 22 downward against the table 22 biased upward by the gas spring 70.

As shown in FIG. 6, the user push-button 50 is disposed in front of the table 22. Specifically, the user push-button 50 is disposed below a center of the front handle 34F in the lateral direction. Therefore, a user can adjust the height of the table 22 by pressing the user push-button 50 with a thumb in a state where a hand is placed on, for example, a left portion or a right portion of the front handle 34F.

Here, as shown in FIG. 6, the cart 20 includes an apparatus push-button 82. The apparatus push-button 82 is provided to protrude from an upper surface of the table 22. The apparatus push-button 82 is provided at the front portion 22A of the table 22 and protrudes from an opening 41 formed in the top plate 40. As shown in FIG. 7, in a case where the ultrasound diagnostic apparatus 12 is placed on the table 22, the apparatus push-button 82 is pressed by the ultrasound diagnostic apparatus 12.

Figure 10:
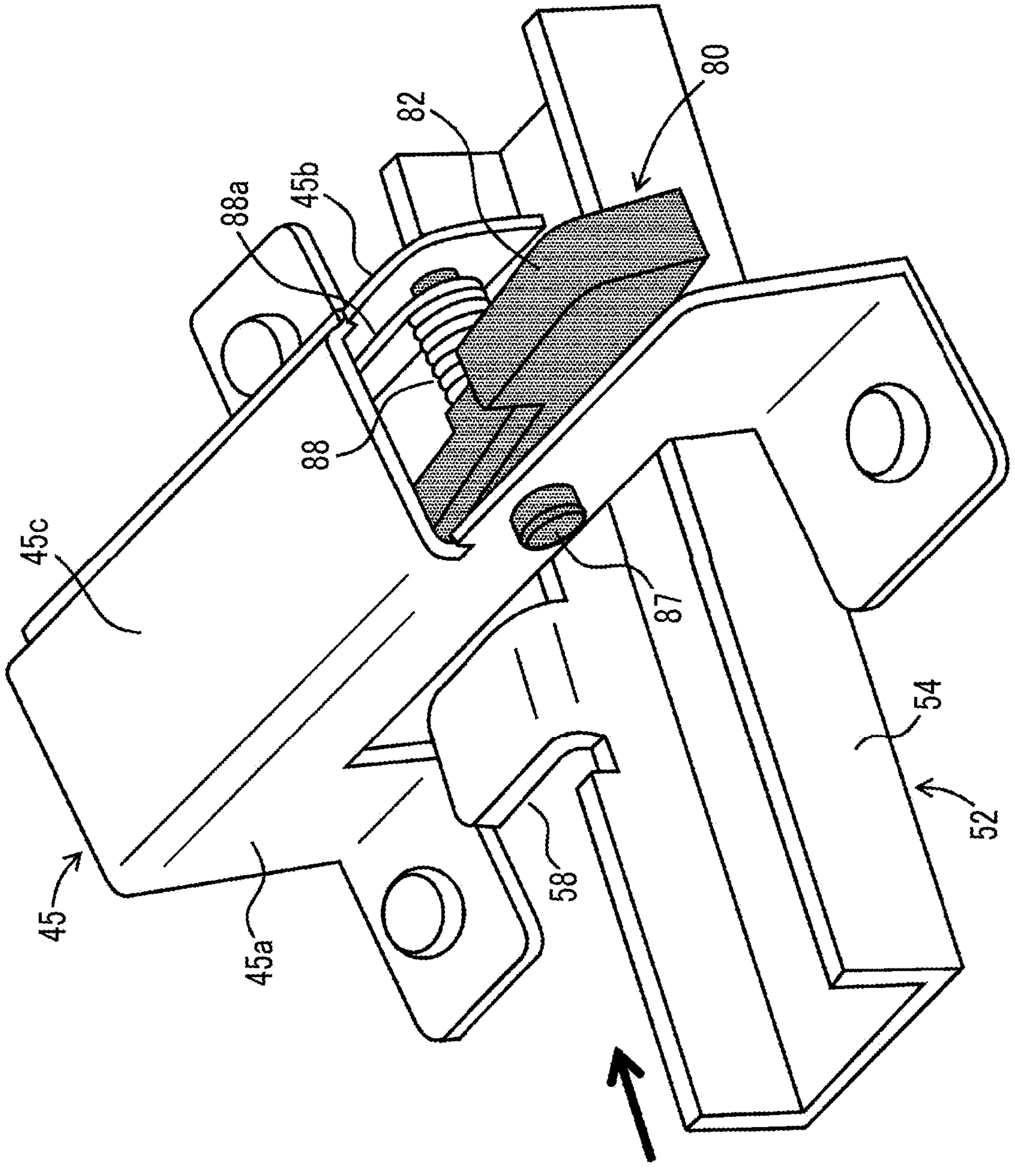
FIG. 10 is a perspective view showing a swinging body.
Figure 11:
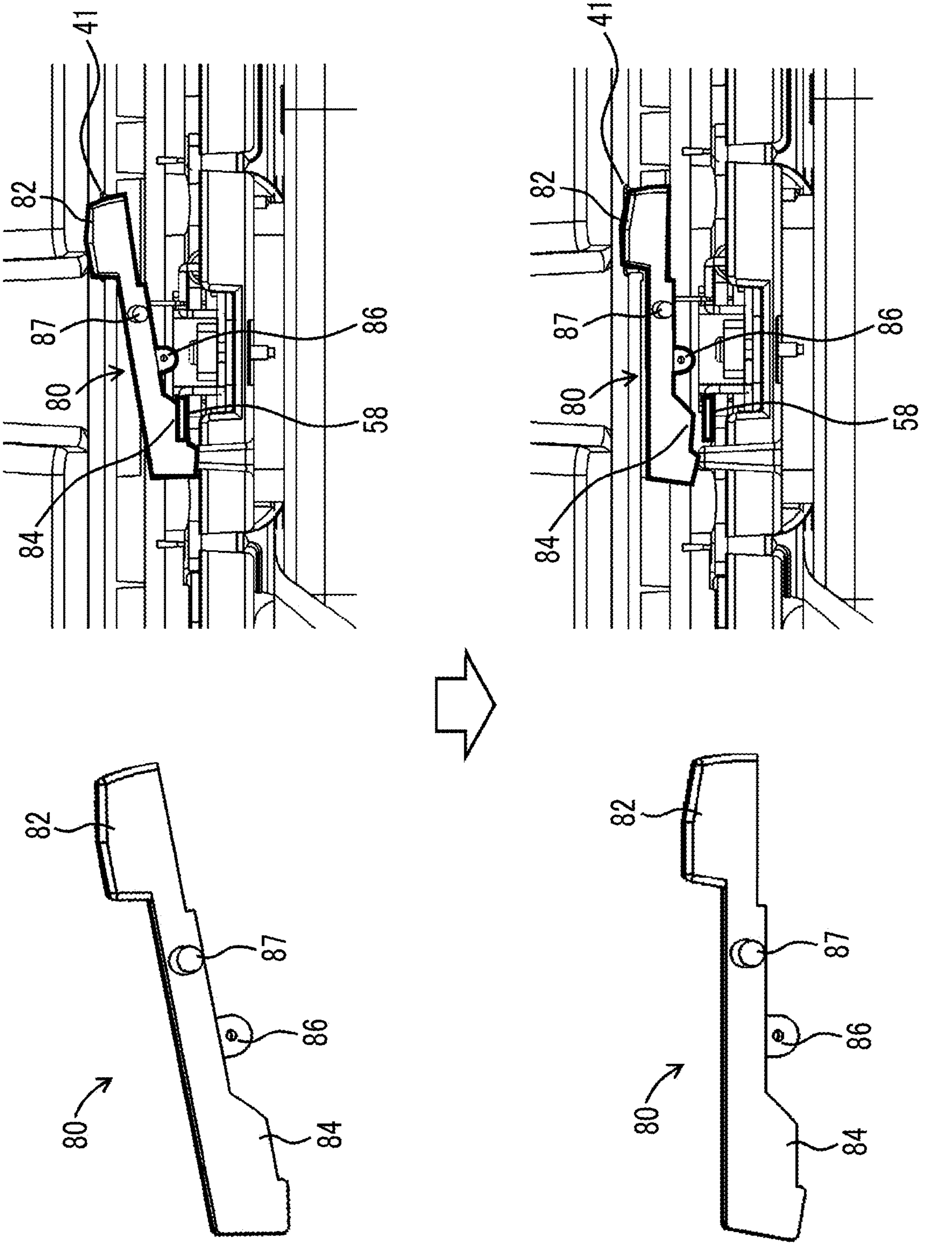
FIG. 11 shows front views showing the swinging body and shows a state before the pressing of an apparatus push-button and a state after the pressing of the apparatus push-button.

FIG. 10 is a perspective view showing a swinging body 80 disposed inside the table, and regarding the translational movement component 54, only a portion of the translational movement component 54 that is near the swinging body 80 is shown in FIG. 10. FIG. 11 shows front views showing the swinging body 80 only and front views showing the swinging body 80 in the table 22 side by side, the upper drawings show a posture in which the swinging body 80 is before the apparatus push-button 82 is pressed and the lower drawings show a posture in which the swinging body 80 is after the apparatus push-button 82 is pressed. The swinging body 80 is swingable around a support shaft 87. The swinging body 80 includes the apparatus push-button 82 provided on one side with respect to the support shaft 87. In addition, the swinging body 80 includes a movement restriction portion 84 that is provided on a side opposite to the one side with respect to the support shaft 87.

As shown in FIG. 10, the cart 20 includes a holding portion 45 that swingably holds the swinging body 80. The holding portion 45 is fixed to the housing 38 of the table 22. The holding portion 45 is provided over the translational movement component 54. The holding portion 45 includes two side plates 45*a* and 45*b* facing each other and a top plate 45*c* that connects upper portions of the two side plates 45*a* and 45*b* to each other.

The swinging body 80 is disposed between the two side plates 45*a* and 45*b*. The support shaft 87 of the swinging body 80 is held by the two side plates 45*a* and 45*b* such that the swinging body 80 can swing. A torsion spring 88 serving as a biasing member is disposed on an outer periphery of the support shaft 87 between the two side plates 45*a* and 45*b*. One end 88*a* of the torsion spring 88 comes into contact with a lower surface of the top plate 45*c*. The other end of the torsion spring 88 is hooked at a hole of a spring hooking portion 86 (refer to FIG. 11) of the swinging body 80. The swinging body 80 forms an unpressed state of the apparatus push-button 82 by being biased in a certain rotation direction around the support shaft 87 by the torsion spring 88.

As shown in FIG. 10, the translational movement component 54 includes a protruding portion 58 that protrudes in a direction intersecting a movement direction (refer to a thick arrow in FIG. 10) of the translational movement component 54. In this embodiment, the protruding portion 58 protrudes outward from the body of the translational movement component 54. The protruding portion 58 may protrude toward the inside of the body of the translational movement component 54 or may protrude upward from the body of the translational movement component 54.

As shown in the upper drawings of FIG. 11, in a case where the apparatus push-button 82 is in the unpressed state, the apparatus push-button 82 protrudes from the upper surface of the table 22 and the movement restriction portion 84 restricts movement of the protruding portion 58 of the translational movement component while being positioned in a region in which the movement restriction portion 84 interferes with the movement of the protruding portion 58. Meanwhile, in a case where the ultrasound diagnostic apparatus 12 is placed on the table 22 and the apparatus push-button 82 is pressed by the ultrasound diagnostic apparatus 12, as shown in the lower drawings of FIG. 11, the swinging body 80 swings against a biasing force of the torsion spring 88 and the movement restriction portion 84 allows movement of the protruding portion 58 of the translational movement component while being positioned in a region in which the movement restriction portion 84 do not interfere with the movement of the protruding portion 58. In addition, in a case where the ultrasound diagnostic apparatus 12 is removed from the table 22, the swinging body 80 is caused to restore an original posture (the upper drawings in FIG. 11) by the biasing force of the torsion spring 88. As described above, the movement restriction portion 84 is interlocked with the apparatus push-button 82 via a seesaw structure. Note that refer to FIGS. 7 and 9 because the positions of the swinging body 80 and the protruding portion 58 are shown in FIGS. 7 and 9 as well.

According to such a configuration, in a case where the ultrasound diagnostic apparatus 12 is not placed on the table 22, the apparatus push-button 82 is in the unpressed state and the movement restriction portion 84 restricts movement of the translational movement component 54. Therefore, even in a case where the user push-button 50 is pressed, the movement of the user push-button 50 being pressed is not transmitted to the gas spring button 74. Therefore, in a case where the ultrasound diagnostic apparatus 12 is not placed on the table 22, an operation performed on the user push-button 50 has no effect and the table 22 can be prevented from being rapidly raised against the intention of a user. In addition, since the apparatus push-button 82 and the movement restriction portion 84 are realized by the swinging body 80, the structure can be simplified.

In a state where the ultrasound diagnostic apparatus 12 is not on the table 22, a user may raise and lower the table 22 by pressing the user push-button 50 while pressing the apparatus push-button 82.

Figure 12:
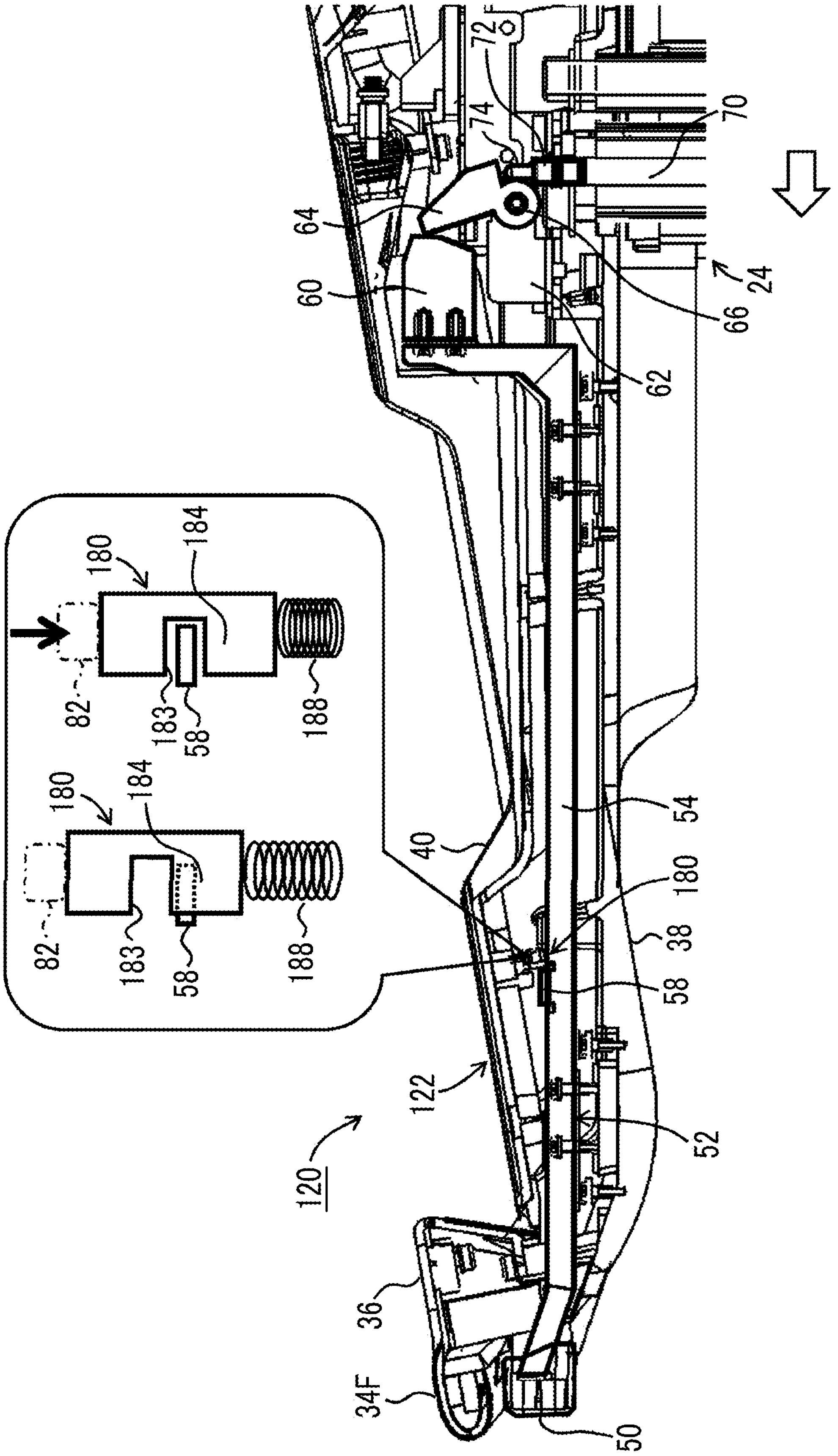
FIG. 12 is a cross-sectional view showing the inside of a table according to another embodiment and shows a configuration of a moving body, which is shown in a balloon.

FIG. 12 is a cross-sectional view showing the inside of a table 122 according to another embodiment and shows a configuration of a moving body 180, which is shown in a balloon. In this embodiment, the moving body 180 is used instead of the above-described swinging body 80. In the bubble of FIG. 12, the moving body 180 as seen from a rear surface (a direction along an outlined arrow in FIG. 12) is schematically shown.

The cart 120 includes the moving body 180. The moving body 180 is held by a holding portion (not shown) fixed inside the table 122 such that the moving body 180 is movable in a vertical direction. The moving body 180 is a plate-shaped member having a rectangular shape that is long in the vertical direction as seen in a rear view. The moving body 180 is provided with a notch 183 through which the protruding portion 58 of the translational movement component 54 passes. The moving body 180 is connected to the apparatus push-button 82. A portion of the moving body 180 that is below the notch 183 functions as a movement restriction portion 184.

A compression coil spring 188 serving as a biasing member is disposed below the moving body 180. The moving body 180 is biased upward by the compression coil spring 188 to form the unpressed state of the apparatus push-button 82. Note that a tension coil spring may be provided above the moving body 180 and the moving body 180 may be biased upward by the tension coil spring.

As shown in the left drawing in the balloon of FIG. 12, in a case where the apparatus push-button 82 is in the unpressed state, the apparatus push-button 82 protrudes from the upper surface of the table 122 and the movement restriction portion 184 restricts movement of the protruding portion 58 of the translational movement component 54 while being positioned in a region in which the movement restriction portion 184 interferes with the movement of the protruding portion 58. Meanwhile, in a case where the ultrasound diagnostic apparatus 12 is placed on the table 122 and the apparatus push-button 82 is pressed by the ultrasound diagnostic apparatus 12, as shown in the right drawing in the balloon of FIG. 12, the moving body 180 is lowered against a biasing force of the compression coil spring 188 and the movement restriction portion 184 allows movement of the protruding portion 58 of the translational movement component 54 while being positioned in a region in which the movement restriction portion 184 do not interfere with the movement of the protruding portion 58. That is, the protruding portion 58 becomes able to move through the notch 183 of the moving body 180. In addition, in a case where the ultrasound diagnostic apparatus 12 is removed from the table 122, the moving body 180 is caused to enter an original state (the left drawing in the balloon of FIG. 12) again by the biasing force of the compression coil spring 188. As described above, the movement restriction portion 184 is interlocked with the apparatus push-button 82 via a slide structure.

Even in the case of such a configuration, in a case where the ultrasound diagnostic apparatus 12 is not placed on the table 122, an operation performed on the user push-button 50 has no effect and the table 122 can be prevented from being rapidly raised against the intention of a user. In addition, the apparatus push-button 82 and the movement restriction portion 184 can be realized in a narrow space extending in the vertical direction.

What is claimed is:

1. A cart for an ultrasound diagnostic apparatus with a table on which a transportable ultrasound diagnostic apparatus is placed, the cart comprising:

a gas spring that is able to form a locked state in which the table is unraisable and unlowerable and an unlocked state in which the table is unlocked and is biased upward, wherein the gas spring includes a gas spring operation reception portion that receives an operation of switching between the locked state and the unlocked state, the cart further includes a user push-button, and a movement transmission mechanism that transmits movement of the user push-button being pressed to the gas spring operation reception portion so that a state of the table is changed from the locked state to the unlocked state in a case where the user push-button is pressed, the movement transmission mechanism includes a translational movement component that translationally moves as the user push-button is pressed and that is in charge of at least part of transmission of the movement from the user push-button to the gas spring operation reception portion, the cart further includes an apparatus push-button that is provided to protrude from an upper surface of the table and that is pressed by the transportable ultrasound diagnostic apparatus while the transportable ultrasound diagnostic apparatus is placed on the table, and a movement restriction portion that is interlocked with the apparatus push-button, and the movement restriction portion restricts movement of the translational movement component while being positioned in a region in which the movement restriction portion interferes with the movement of the translational movement component while the apparatus push-button is in an unpressed state and allows the movement of the translational movement component while being positioned in a region in which the movement restriction portion does not interfere with the movement of the translational movement component in a case where the apparatus push-button is in a pressed state.

2. The cart for an ultrasound diagnostic apparatus according to claim 1, wherein the user push-button is disposed in front of the table.

3. The cart for an ultrasound diagnostic apparatus according to claim 1, further comprising:

a front handle that is connected to the table and that is positioned in front of the table, wherein the user push-button is disposed below a center of the front handle in a lateral direction.

4. The cart for an ultrasound diagnostic apparatus according to claim 1, wherein the translational movement component includes a protruding portion that protrudes in a direction intersecting a movement direction of the translational movement component, the cart further includes a swinging body that is swingable around a support shaft, the swinging body includes the apparatus push-button provided on one side with respect to the support shaft and includes the movement restriction portion provided on a side opposite to the one side with respect to the support shaft, the swinging body forms the unpressed state of the apparatus push-button by being biased in a certain rotation direction around the support shaft by a biasing member, in a case where the apparatus push-button is in the unpressed state, the apparatus push-button protrudes from the upper surface of the table and the movement restriction portion restricts movement of the protruding portion of the translational movement component while being positioned in a region in which the movement restriction portion interferes with the movement of the protruding portion, and in a case where the swinging body swings as the apparatus push-button is pressed, the movement restriction portion allows the movement of the protruding portion of the translational movement component while being positioned in a region in which the movement restriction portion does not interfere with the movement of the protruding portion.

5. The cart for an ultrasound diagnostic apparatus according to claim 1, wherein the translational movement component includes a protruding portion that protrudes in a direction intersecting a movement direction of the translational movement component, the cart further includes a moving body that is movable in a vertical direction, the moving body is connected to the apparatus push-button and includes the movement restriction portion, the moving body forms the unpressed state of the apparatus push-button by being biased upward by a biasing member, in a case where the apparatus push-button is in the unpressed state, the apparatus push-button protrudes from the upper surface of the table and the movement restriction portion restricts movement of the protruding portion of the translational movement component while being positioned in a region in which the movement restriction portion interferes with the movement of the protruding portion, and in a case where the moving body is lowered as the apparatus push-button is pressed, the movement restriction portion allows the movement of the protruding portion of the translational movement component while being positioned in a region in which the movement restriction portion does not interfere with the movement of the protruding portion.

6. The cart for an ultrasound diagnostic apparatus according to claim 1, wherein the user push-button is disposed in front of the table, the movement transmission mechanism and the gas spring operation reception portion are disposed in an inner space of the table, the gas spring operation reception portion is a gas spring button that protrudes upward, and the movement transmission mechanism includes a movement direction changing mechanism that converts forward movement of the translational movement component, which is caused in a case where the user push-button is pressed, into downward movement and that transmits the downward movement to the gas spring button.

7. The cart for an ultrasound diagnostic apparatus according to claim 6, further comprising:

a columnar support that supports the table to be raisable and lowerable, wherein the gas spring is disposed in the columnar support, the columnar support includes an upper columnar support to which the table is connected and a lower columnar support that is disposed below the upper columnar support, the columnar support expands and contracts as one of the upper columnar support or the lower columnar support is inserted into the other of the upper columnar support or the lower columnar support, one end of the gas spring is fixed to the table, the other end of the gas spring is fixed to the lower columnar support or a support body disposed below the lower columnar support, and the one end of the gas spring includes the gas spring button that is disposed in the inner space of the table.

8. An ultrasound diagnostic unit comprising:

a cart for an ultrasound diagnostic apparatus with a table on which a transportable ultrasound diagnostic apparatus is placed, the cart comprising:

a gas spring that is able to form a locked state in which the table is unraisable and unlowerable and an unlocked state in which the table is unlocked and is biased upward, wherein the gas spring includes a gas spring operation reception portion that receives an operation of switching between the locked state and the unlocked state, the cart further includes a user push-button, and a movement transmission mechanism that transmits movement of the user push-button being pressed to the gas spring operation reception portion so that a state of the table is changed from the locked state to the unlocked state while the user push-button is pressed, the movement transmission mechanism includes a translational movement component that translationally moves as the user push-button is pressed and that is in charge of at least part of transmission of the movement from the user push-button to the gas spring operation reception portion, the cart further includes an apparatus push-button that is provided to protrude from an upper surface of the table and that is pressed by the transportable ultrasound diagnostic apparatus while the transportable ultrasound diagnostic apparatus is placed on the table, and a movement restriction portion that is interlocked with the apparatus push-button, and the movement restriction portion restricts movement of the translational movement component while being positioned in a region in which the movement restriction portion interferes with the movement of the translational movement component while the apparatus push-button is in an unpressed state and allows the movement of the translational movement component while being positioned in a region in which the movement restriction portion does not interfere with the movement of the translational movement component while the apparatus push-button is in a pressed state; and the transportable ultrasound diagnostic apparatus placed on the table of the cart.

* * * * *